United States Patent
Loseu et al.

(10) Patent No.: US 10,945,617 B2
(45) Date of Patent: Mar. 16, 2021

(54) LOW-COMPLEXITY SENSOR DISPLACEMENT TOLERANT PULSE OXIMETRY BASED HEART RATE MEASUREMENT

(71) Applicant: Texas Instruments Incorporated, Dallas, TX (US)

(72) Inventors: Vitali Loseu, Irving, TX (US); Sourabh Ravindran, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 649 days.

(21) Appl. No.: 15/634,521

(22) Filed: Jun. 27, 2017

(65) Prior Publication Data

US 2017/0296075 A1    Oct. 19, 2017

Related U.S. Application Data

(63) Continuation of application No. 14/166,527, filed on Jan. 28, 2014, now Pat. No. 9,717,423.

(60) Provisional application No. 61/757,897, filed on Jan. 29, 2013, provisional application No. 61/757,505, filed on Jan. 28, 2013.

(51) Int. Cl.
*A61B 5/024* (2006.01)
*A61B 5/00* (2006.01)

(52) U.S. Cl.
CPC .......... *A61B 5/02416* (2013.01); *A61B 5/681* (2013.01); *A61B 5/725* (2013.01); *A61B 5/7207* (2013.01)

(58) Field of Classification Search
None
See application file for complete search history.

(56) References Cited

U.S. PATENT DOCUMENTS

| | | | | |
|---|---|---|---|---|
| 2005/0240087 A1* | 10/2005 | Keenan | ................. | A61B 5/725 600/301 |
| 2006/0036183 A1* | 2/2006 | Sackner | ............... | A61B 5/0535 600/481 |

(Continued)

OTHER PUBLICATIONS

Kali Vara Prasad Naraharisetti and Manan Bawa, "Comparison of Different Signal Processing Methods for Reducing Artifacts from Photoplethysmograph Signal", 2011 IEEE International Conference on Electro/Information Technology (EIT), May 15-17, 2011, Mankato, MN, pp. 1-8.

(Continued)

*Primary Examiner* — Etsub D Berhanu
(74) *Attorney, Agent, or Firm* — Ray A. King; Charles A. Brill; Frank D. Cimino

(57) ABSTRACT

Methods for heart rate measurement based on pulse oximetry are provided that can tolerate some degree of relative displacement of a photoplethysmograph (PPG) heart rate monitor device. In some methods, artifact compensation based on a reference signal is performed on the PPG signal data to remove artifacts in the signal that may be caused, for example, by changes in ambient light and/or motion of a person wearing the monitor device. The reference signal used for artifact compensation may be generated using an LED of a complementary wavelength to that of the LED used to generate the PPG signal, or by driving an LED at a lower current than the current applied to generate the PPG signal.

5 Claims, 11 Drawing Sheets

(56) References Cited

U.S. PATENT DOCUMENTS

| | | |
|---|---|---|
| 2006/0106294 A1 | 5/2006 | Maser et al. |
| 2007/0106137 A1 | 5/2007 | Baker et al. |
| 2008/0076988 A1 | 3/2008 | Sarussi et al. |
| 2009/0203972 A1 | 8/2009 | Heneghan et al. |
| 2010/0016738 A1* | 1/2010 | Addison ............ A61B 5/02416 600/500 |
| 2010/0106220 A1 | 4/2010 | Ecker et al. |
| 2012/0190947 A1 | 7/2012 | Chon et al. |
| 2013/0085354 A1 | 4/2013 | Hete et al. |
| 2013/0253334 A1 | 9/2013 | Al-Ali et al. |
| 2013/0253341 A1 | 9/2013 | Sethi et al. |
| 2013/0261415 A1 | 10/2013 | Ashe et al. |
| 2013/0267854 A1 | 10/2013 | Johnson et al. |
| 2013/0289413 A1 | 10/2013 | Ochs et al. |
| 2013/0296666 A1 | 11/2013 | Kumar et al. |
| 2014/0235979 A1* | 8/2014 | Banet ................... A61B 5/6822 600/324 |

OTHER PUBLICATIONS

Lei Wang, et al, "Multichannel Reflective PPG Earpiece Sensor with Passive Motion Cancellation", IEEE Transactions on Biomedical Circuits and Systems, vol. 1, No. 4, Dec. 2007, pp. 235-240.

Andreas Caduff, "How vendors deal with the lack of integration—yesterday, today, tomorrow", World Medtech Forum Luceme, Sep. 17-29, 2013, Luzern, Switzerland, pp. 1-20.

M. Raghu Ram et al, "On the Performance of Time Varying Step-size Least Mean Squares (TVS-LMS) Adaptive Filter for MA Reduction from PPG Signals", 2011 International Conference on Communication and Signal Processing (ICCSP), Feb. 10-12, 2011, Kerala, India, pp. 431-435.

Sukor et al. Signal quality measures for pulse oximetry through waveform morphology analysis. Physiol. Meas. 32 (2011) 369-384.

* cited by examiner

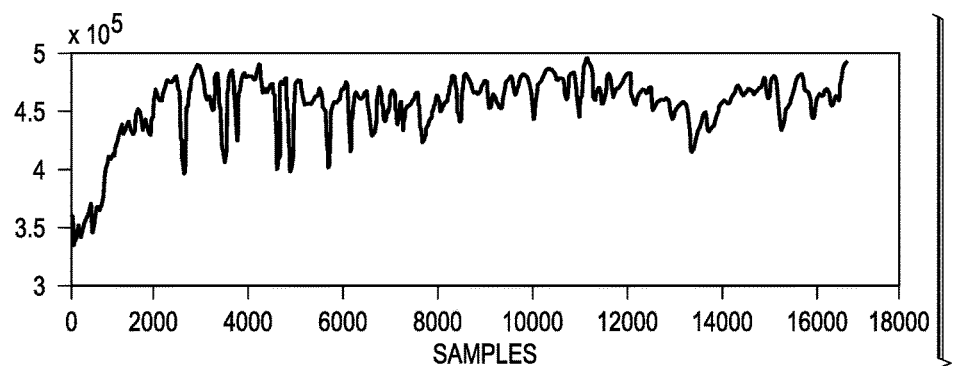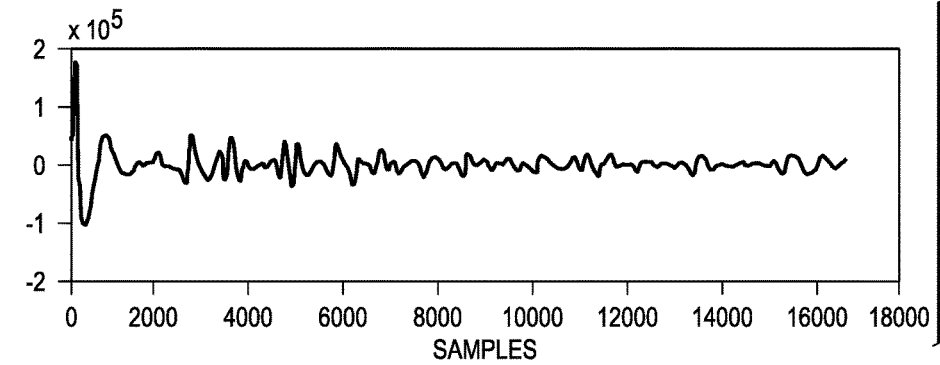
FIG. 5
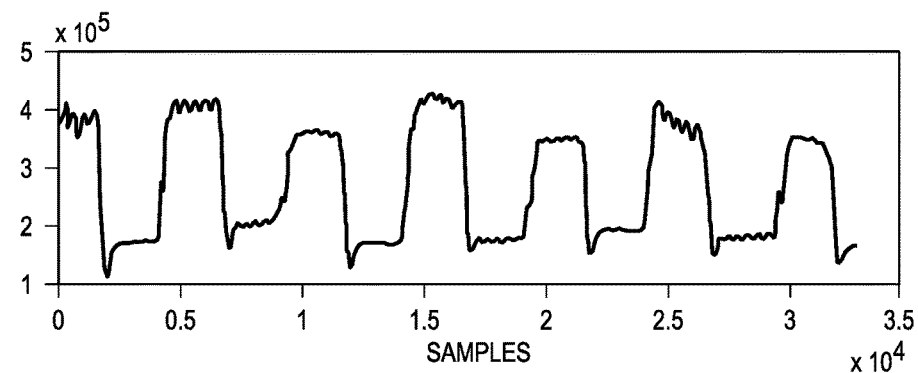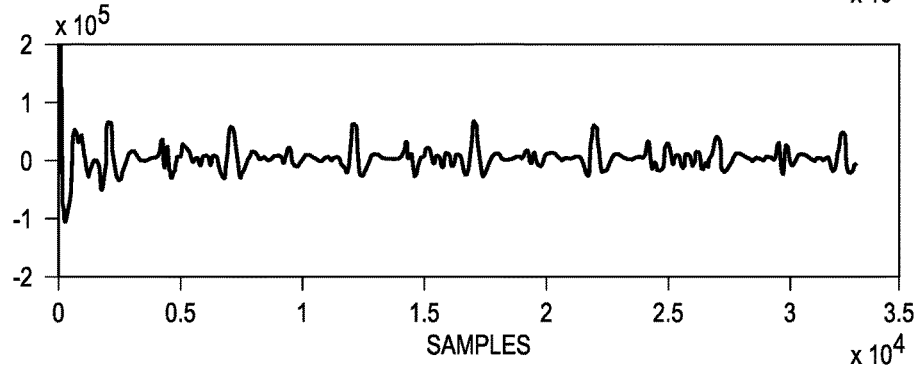
FIG. 6

LOW-COMPLEXITY SENSOR DISPLACEMENT TOLERANT PULSE OXIMETRY BASED HEART RATE MEASUREMENT

CROSS-REFERENCE TO RELATED APPLICATIONS

Under 35 U.S.C. §§ 119(e), 120, this continuation application claims benefits of and priority to U.S. patent application Ser. No. 14/166,527 (TI-73170), filed on Jan. 28, 2014, which claims the benefit of and priority to U.S. Provisional Patent Application Ser. No. 61/757,505, filed on Jan. 28, 2013, and U.S. Provisional Patent Application Ser. No. 61/757,897, filed on Jan. 29, 2013. The entirety of the above referenced applications are hereby incorporated by reference herein in their entirety.

BACKGROUND OF THE INVENTION

Field of the Invention

Embodiments of the present invention generally relate heart rate measurement and more specifically relate to pulse oximetry based heart rate measurement that is tolerant to sensor displacement.

Description of the Related Art

Heart rate measurement is an important problem in the context of many applications including medical monitoring, sports training, and fitness. Traditionally, heart rate monitoring has been performed in a static medical setting by trained professionals. However, recent trends in sports and fitness have created a demand for effective unsupervised heart rate monitoring in an uncontrolled environment. The demand for continuous monitoring suggests that the device used to measure the heart rate should be wearable and seamless. A watch-like form factor is suitable for these requirements since this form factor is a commonly used form factor for heart rate monitoring during sports or fitness training. Further, the use of light (visible or otherwise) as the sensing modality may have fewer limitations than traditional approaches like electrocardiogram (EKG) in a wrist mounted device as there may not be sufficient distance between the electrodes to obtain a good EKG signal.

Pulse oximetry is a commonly used noninvasive light-based technique for measuring the oxygen saturation level of arterial blood and pulse (heart rate). Typically, the sensor portion of a pulse oximeter passes light through blood perfused tissue, e.g., a finger or an ear lobe, and photoelectrically senses the absorption of light in the tissue. Arteries expand and contract due to blood flow and, thus, the amount of absorbed light changes in the course of a heart beat. The resulting signal is referred to as a photoplethysmograph (PPG). The PPG signal may be analyzed to determine, among other thing, the heart rate of the person to which the PPG sensor is attached.

Typical pulse oximetry techniques assume that the person to whom the PPG sensor is attached is relatively stationary and motionless. Thus, such techniques may not account for motion artifacts and relative displacement of the sensor when analyzing the PPG signal. Many approaches have been proposed to address motion artifacts in PPG signals including adaptive filtering with a reference of an additional sensor, e.g., an accelerometer, and different statistical learning models. Some such approaches are described in L. Wang, et al., "Multichannel Reflective PPG Earpiece Sensor With Passive Motion Cancellation," Biomedical Circuits and Systems, IEEE Transactions on, Vol. 1, No. 4, pp. 235-241, December 2007, M. R. Ram, et al., "On the Performance of Time Varying Step-Size Least Mean Squares (TVS-LMS) Adaptive Filter for MA Reduction from PPG Signals," Communications and Signal Processing (ICCSP), 2011 International Conference on, pp. 431-435, February 2011, and K. Naraharisetti, et al., "Comparison of Different Signal Processing Methods for Reducing Artifacts from Photoplethysmograph Signal," Electro/Information Technology (EIT), 2011 IEEE International Conference on, pp. 1-8, May 2011. None of these approaches, however, address the issue of relative sensor displacement, i.e., changes in position or orientation of the sensor. In addition, the proposed approaches for removing motion artifacts need improvement.

SUMMARY

Embodiments of the present invention relate to methods, apparatus, and computer readable media for pulse oximetry based heart rate measurement. In one aspect, a method for heart rate measurement in a photoplethysmograph (PPG) heart rate monitor device is provided that includes capturing a PPG signal using a first light emitting diode (LED) of the PPG heart rate monitor device, capturing a reference signal using a second LED of the PPG heart rate monitor device, wherein a current used to drive the second LED is lower than a current used to drive the first LED, using the reference signal to remove motion noise from the PPG signal, wherein a motion noise compensated PPG signal is generated, and estimating a heart rate using the motion noise compensated PPG signal.

In one aspect, a method for heart rate measurement in a photoplethysmograph (PPG) heart rate monitor device is provided that includes capturing a PPG signal using a first light emitting diode (LED) of the PPG heart rate monitor device, capturing a reference signal using a second LED of the PPG heart rate monitor device, wherein a wavelength of the second LED is complementary to a wavelength of the first LED, using the reference signal to remove motion noise from the PPG signal, wherein a motion noise compensated PPG signal is generated, and estimating a heart rate using the motion noise compensated PPG signal.

In one aspect, a method for heart rate measurement in a photoplethysmograph (PPG) heart rate monitor device is provided that includes capturing a PPG signal using a first light emitting diode (LED) of the PPG heart rate monitor device, determining whether or not a first portion of the PPG signal includes displacement noise, discarding the first portion of the PPG signal when the first portion includes displacement noise, and using the first portion of the PPG signal for heart rate measurement when the first portion does not include displacement noise.

BRIEF DESCRIPTION OF THE DRAWINGS

Particular embodiments will now be described, by way of example only, and with reference to the accompanying drawings:

FIGS. 4-7 are graphs illustrating various concepts of the heart rate measurement method.

DETAILED DESCRIPTION OF EMBODIMENTS OF THE INVENTION

Figure 1:
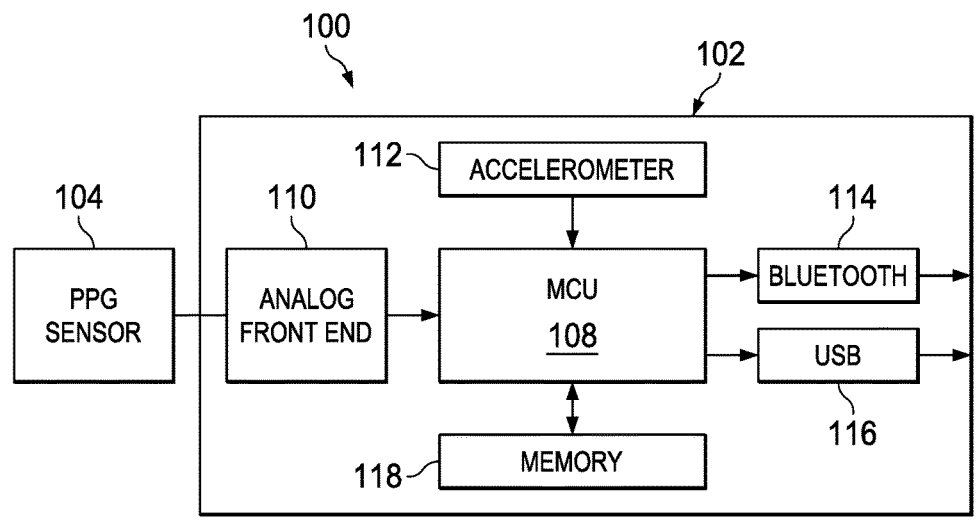
FIG. 1 is a block diagram of an example photoplethysmograph (PPG) heart rate monitor unit.

Specific embodiments of the invention will now be described in detail with reference to the accompanying figures. Like elements in the various figures are denoted by like reference numerals for consistency.

Example embodiments of the invention provide for heart rate measurement using a single PPG sensor in a photoplethysmograph (PPG) heart rate monitor unit worn on the wrist. The heart rate measurement technique used can tolerate some degree of relative displacement of the PPG sensor. More specifically, portions of the PPG signal data that correspond to periods of significant sensor displacement are identified and discarded from the heart rate estimation in order to maintain a robust heart rate estimate.

Further, in some embodiments, artifact compensation based on a reference signal is performed on the PPG signal data to remove artifacts in the signal that may be caused, for example, by changes in ambient light and/or motion of the person wearing the monitor unit. In some embodiments, the reference signal used for artifact compensation is generated by lowering the current applied to the light emitting diode (LED) used to generate the PPG signal. In some embodiments, the reference signal used for artifact compensation is generated by a secondary (LED) driven by a significantly lower current than the primary LED used to generate the PPG signal. In some embodiments, the reference signal used for artifact compensation is generated using an LED of a complementary wavelength to that of the LED used to generate the PPG signal. Generation of reference signals is described in more detail herein.

Figure 2:
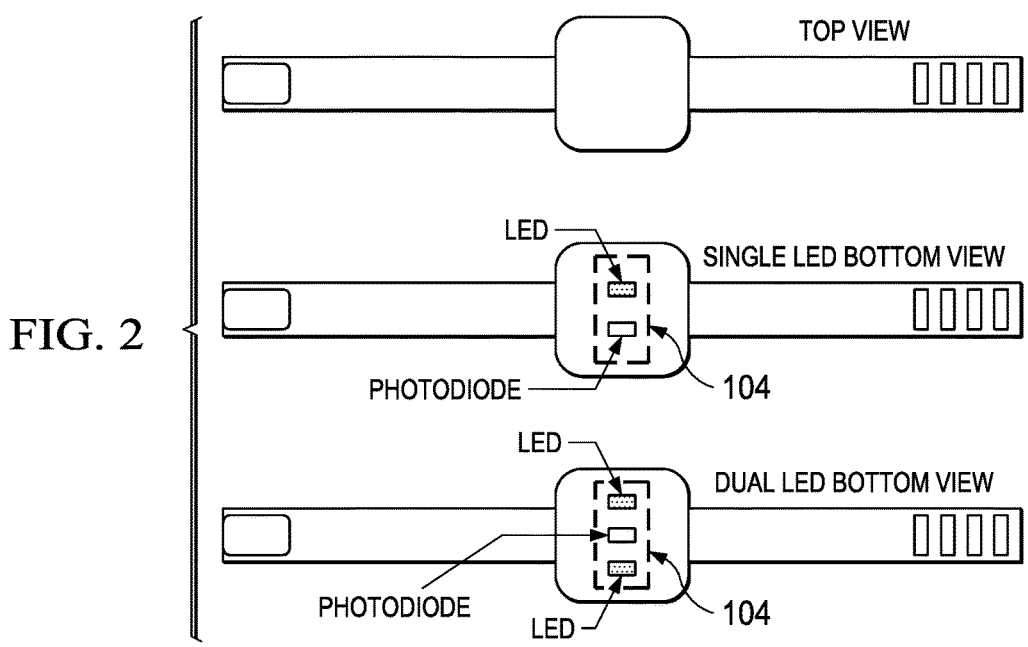
FIG. 2 is an example form factor for housing the PPG heart rate monitor unit of FIG. 1.

FIG. 1 is a block diagram of an exemplary photoplethysmograph (PPG) heart rate monitor unit 100 suitable for heart rate monitoring in a watch-like form factor such as that of FIG. 2. The PPG heart rate monitor unit 100 includes a PPG sensor component 104 configured to capture a PPG signal from the person wearing the monitor unit and a processing component 102 configured to process the PPG signal to measure the heart rate of a person wearing the monitor unit.

In some embodiments, the PPG sensor component 104 includes a single light emitting diode (LED) arranged to pass light through a blood vessel in the wrist and a single photodiode arranged to detect the wavelength of the light from the LED after it passes through the blood vessel. In some embodiments, the PPG sensor component 104 includes two LEDs, a primary LED and a secondary LED, and a single photodiode arranged to detect the wavelengths of the light from both LEDs after it passes through a blood vessel. In such embodiments, the primary LED is arranged to pass light through a blood vessel in the wrist for PPG signal generation and the secondary LED is arranged to pass light through the blood vessel to generate a reference signal for artifact compensation. In some such embodiments, the secondary LED has a wavelength complementary to that of the primary LED. In other such embodiments, the primary LED is driven at a current sufficient to penetrate the blood vessel to the extent needed to sense the pulsatile component (the component corresponding to the heart pulse) while the secondary LED is driven at a much lower current to sense ambient light and motion while not picking up a significant amount (or none) of the pulsatile component.

An LED or LEDs producing light of any suitable wavelength, e.g., red, infrared, blue, etc., may be used. In some single LED PPG sensor embodiments, the single LED is an infrared LED. In some two LED PPG sensor embodiments, the primary LED is an infrared LED and the secondary LED is an LED producing light at a complementary wavelength, e.g., red or green. In some two LED PPG sensor embodiments, the primary LED and the secondary LED produce light at the same wavelength.

The processing component 102 includes a microcontroller (MCU) 108, an accelerometer 112, a Bluetooth transceiver 114, an analog front end (AFE) 110, and memory 118. The MCU 108 may be any suitable microcontroller, such as, for example, an MSP430 device available from Texas Instruments, Inc. The MCU 108 includes memory that can be used to store software instructions to perform heart rate measurement as described herein. Memory 118 may be any suitable memory device or devices, such as, for example, one or more ferroelectric random access memory (FRAM) devices. Memory 118 is coupled to the MCU 108 and may be used, for example, to store data used in the execution of the heart rate monitoring and to store a heart rate history.

The accelerometer 112 is coupled to the MCU 108 via an interface provided by the MCU 108 and provides data regarding the motion of a person wearing the monitor unit 100. The accelerometer 112 may be, for example, any suitable three axis accelerometer.

The Bluetooth transceiver 114 is coupled to the MCU 108 and may be used, for example, to transfer the computed heart rate measurement of a person wearing the monitor unit 100 to another device for display and/or further processing. For example, the heart rate measurement may be transmitted to a smart phone or other personal digital assistant, a laptop computer, a desktop computer, a medical monitoring device, etc. The Bluetooth transceiver 114 may be any suitable Bluetooth device, such as, for example, a CC25xx Bluetooth system-on-a-chip (SOC) available from Texas Instruments, Inc.

The USB (universal serial bus) transceiver 116 is coupled to the MCU 108 and may be used, for example, to transfer the computed heart rate measurement of a person wearing the monitor unit 100 to another device for display and/or further processing. For example, the heart rate measurement may be transmitted to a smart phone or other personal digital assistant, a laptop computer, a desktop computer, a medical monitoring device, etc. The associated USB port may also be used to charge a battery (not shown) in the monitor unit 100.

The AFE 110 is coupled to the MCU 108 and the PPG sensor component 104 and provides a control interface between the MCU 108 and PPG sensor component 104. The AFE 110 includes functionality to receive a PPG signal from the PPG sensor component 104, convert the signal to a digital signal, apply analog signal conditioning such as changing the gain of the signal, and provide the digital PPG signal to the MCU 108 for heart rate measurement. The AFE 110 also includes functionality to drive current to one or more LEDs in the PPG sensor 104 as directed by the MCU 108. The particular current to be used and the timing of when to apply the current may be controlled by the MCU 108. The AFE 110 may be any suitable AFE device, such as, for example, the AFE4400 provided by Texas Instruments, Inc.

In some embodiments, the PPG heart rate monitor unit 100 includes a display component (not shown) coupled to the MCU 108. The display component may be used to display the heart rate of a person wearing the monitor unit 100.

FIG. 2 shows an example watch-like form factor suitable for housing a PPG heart rate monitor unit such as that of FIG. 1. Particularly, a top view of the watch-like form factor and two alternate bottom views are shown. The bottom views illustrate, respectively, an example placement of a single LED embodiment of the PPG sensor 104 and a dual LED embodiment of the PPG sensor 104. In the single LED bottom view, the PPG sensor 104 is arranged such that the single LED and the photodiode are exposed on the bottom side of the watch-like form factor. In the dual LED bottom view, the PPG sensor 104 is arranged such that both LEDs and the photodiode are exposed on the bottom side of the watch-like form factor. The watch-like form factor may be worn by a person such that the exposed LED or LEDs and photodiode are centrally placed on the top of the person's wrist such that the sensor 104 can sense the pulsatile flow in the wrist. Alternatively, the watch-like form factor may be worn with the exposed LED and LEDs centrally placed on the bottom of the person's wrist. If the PPG heart rate monitor unit includes an integrated display device, the top view of the watch-like form factor may include a suitably sized opening for the display device.

Figure 3:
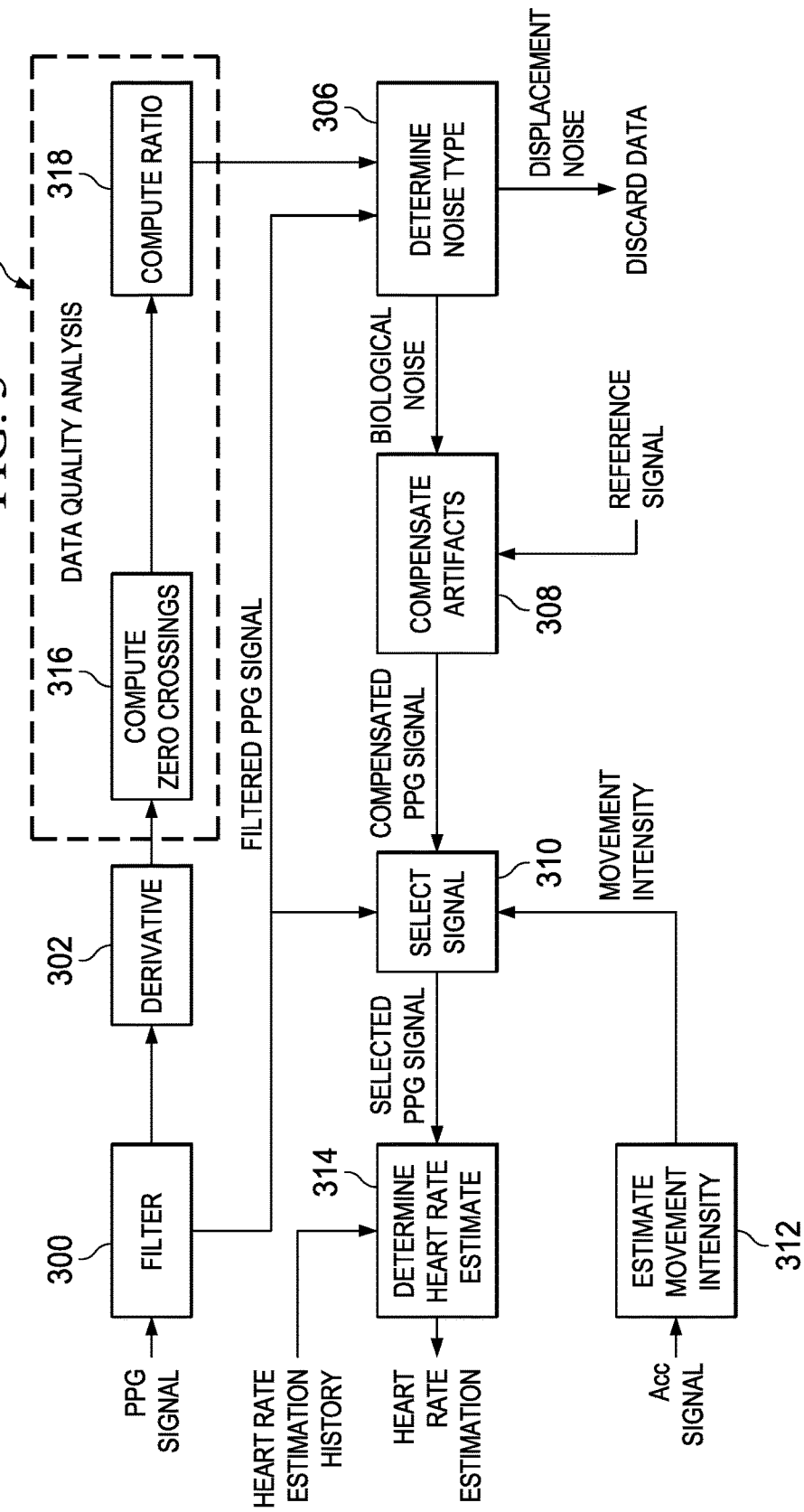
FIGS. 3, 8, 9, 12, 14, 15, 17, and 19 are flow diagrams of a method for heart rate measurement that may be performed by a PPG heart rate monitor unit such as that of FIG. 1.

FIGS. 3, 8, 9, 12, 14, 15, 17, and 19 are flow diagrams of a method for heart rate measurement that may be performed by a PPG heart rate monitor unit such as that of FIG. 1. More specifically, FIG. 3 is a flow diagram illustrating the overall flow of the heart rate measurement signal processing and FIGS. 8, 9, 12, 14, 15, 17, and 19 provide more detail regarding various aspects of the heart rate measurement signal processing. For simplicity of explanation, the method is described relative to the example PPG heart rate monitor unit of FIG. 1. One of ordinary skill in the art will understand that method embodiments are not limited to the particular monitor unit of FIG. 1.

The heart rate estimation method does not attempt to strictly recognize every single heart beat. Rather, the method is based on the idea that some pulses may be contaminated by relative displacement artifacts that may not be recoverable. As is explained in more detail herein, this issue is addressed in part by evaluating the quality of the PPG signal data and in part by evaluating the quality of each individual detected heart pulse. Based on these evaluations, the method selects a subset of pulses from the PPG signal data to be used in the estimation of the heart rate.

Figure 4:
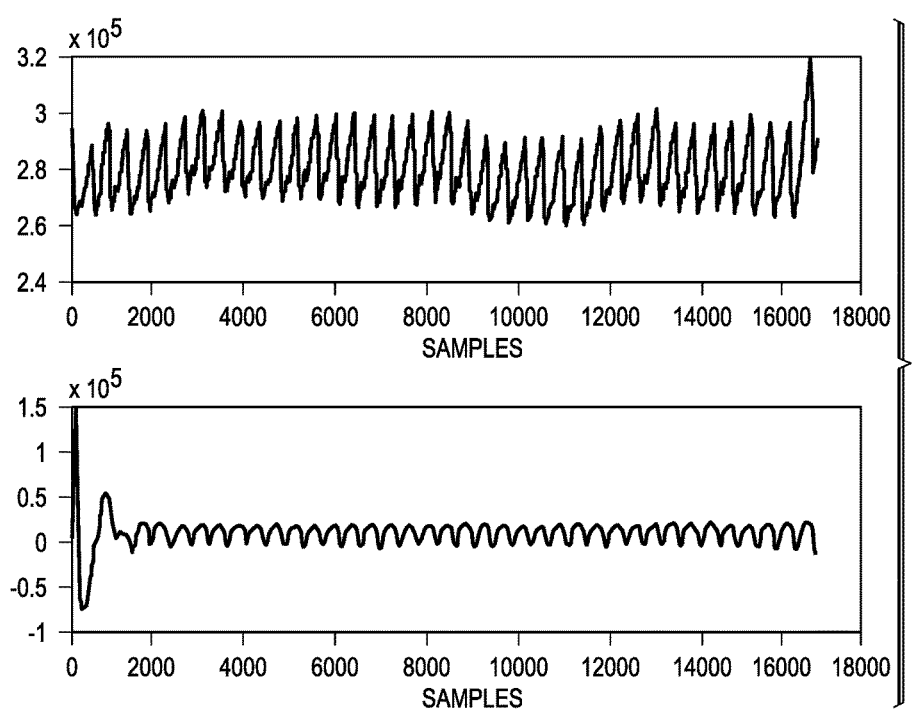

Referring first to FIG. 3, the raw PPG signal data received from the PPG sensor 104 via the AFE 110 is first filtered 300 to focus on the frequency band in the signal having the pulsatile component. The filter used may be, for example, a bandpass filter such as a $3^{rd}$ order Butterworth bandpass filter between 0.5 Hz (Hertz) and 4 Hz. FIG. 4 shows example graphs illustrating filtering results using a Butterworth filter. The top graph illustrates a PPG signal corresponding to an infrared LED and the bottom graph illustrates the signal data after the filter is applied. The filtering may also remove some ambient noise, e.g., ambient noise in the 50-60 Hz range, and noise introduced by a charger.

Human movements and relatively slow sensor displacement take place in the same frequency band. This notion is demonstrated in the graphs of FIG. 5. The top graph illustrates a PPG signal sample in the presence of random movement and relative sensor displacement. The bottom graph illustrates the signal data after the filter is applied. As this bottom graph shows, it is possible to detect heart pulses in the filtered signal but the pulses are not as pronounced and symmetric as those shown in the bottom graph of FIG. 4. Thus, filtering alone will not necessarily yield signal data for reliable heart rate estimation.

Referring again to FIG. 3, the first derivative of the filtered PPG signal is taken 302 and data quality analysis 304 is performed on the resulting data. In general, the data quality analysis 304 analyzes the data to determine whether or not noise due to physical displacement of the PPG sensor 104 (relative to the original placement) is present. Displacement of the senor 104 changes the nature of the PPG signal. For example, FIG. 6 shows graphs illustrating the PPG signal resulting from rotating a finger mounted pulse oximeter clip 90 degrees about the finger every 5 seconds. This rotation results in three distinct positions of the clip. In this experiment, the LED light shined on the finger from the top, left, and right. The top graph shows the raw signal and the bottom graph shows the filtered signal.

The raw PPG signal data clearly shows the three distinct positions. The signal portions that appear flat around $2*10^5$ represent the signal when the sensor is shining top down. The other two positions result in a signal slightly above and slightly below $4*10^5$. The difference comes from the fact that the finger was not symmetrically shaped on the left and right. The left side of the subject's finger was slightly more curved which allowed more light to go through. This experiment demonstrates two ideas.

First, the amount of measured light depends on the geometry of the finger. For simplicity, the total light absorption in the finger from a perspective i, where a perspective is defined as a physical location and orientation of the LEDs and photodiodes, can be represented as the sum of blood absorption, tissue absorption, and bone absorption:

$$\text{Absorption}_{total}^i = \text{Absorption}_{blood}^i + \text{Absorption}_{tissue}^i + \text{Absorption}_{bone}^i.$$

When the sensor is displaced, meaning that the perspective is changed from i to j, each of the absorption components will change. The blood absorption components of the different perspectives are not the same when a displacement takes place; however, they are both highly correlated to the heart rate. This can be seen in top graph of FIG. 6, where the amplitude changes in the signal have different shapes and amplitudes at different DC levels, but very similar periods. The tissue and bone absorption properties are unclear in the context of the optics of the human body. However, they are consistent for any given position of the clip.

Second, a transition between two different orientations of the clip can be thought of as a transition from the perspective i to the perspective j for tissue and bone absorption:

$$\text{Absorption}_{tissue}^i + \text{Absorption}_{bone}^i \rightarrow \text{Absorption}_{tissue}^j + \text{Absorption}_{bone}^j.$$

This transition is not instantaneous, which means that for the duration of the transition, the observed signal corresponds to the samples of perspectives on the path from perspective i to perspective j. Note that many perspectives will produce observations that are similar due to their physical proximity. Transitions have significant effect on the data when they have a very high slope which indicates a sharp transition over a short period of time.

Referring again to FIG. 3, these ideas form the basis for the data quality analysis 304. The structure of the PPG signal in cases of the rapid transition from perspective i to perspective j may be used to detect portions of the signal that contain a higher number of such transitions so that such portions of the signal may be treated as noisy. As the experiment illustrates, a significant relative displacement of the PPG sensor will result in a sharp slope transition in the PPG signal. The zero crossings in the signal may be used to identify periods in the signal data corresponding to rapid transitions, i.e., displacement.

More specifically, to perform data quality analysis 304, first the zero crossings in the derivative data of the filtered PPG signal are computed 316. Two sets of zero crossing data are extracted in order to verify the slope. One set approximates a derivative value to be zero when the value is between [−a, a], while the other approximates the derivative value to zero when the value is between [−b, b], where b>a. The intervals [−a, a] and [−b, b] may be referred to as threshold intervals herein. The values of a and b are implementation dependent and may be empirically determined. The particular values may depend on the particular LED and photodiode used in the PPG sensor. In some embodiments, a=10 and b=15.

Figure 7:
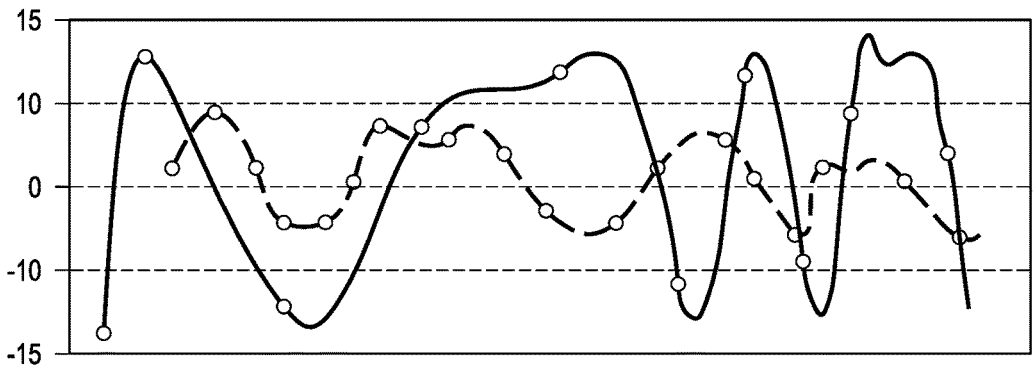

Since b is a larger threshold, it can capture sharper transitions in the signal that are otherwise missed by the threshold a, as demonstrated in FIG. 7. Note that this figure assumes b=15 and a=10. The dots on the curves correspond to points captured by the intervals. The [−10, 10] threshold can capture all of the points in the dotted curve and the [−15, 15] threshold captures the points in the solid curve as well as the points in the dotted curve.

Referring again to FIG. 3, the ratio of the number of zero crossings captured by the threshold a and the number of zero crossing captured by the threshold b in a window of data is computed 318. The size of the data window may be implementation dependent and may be determined empirically. This ratio is an indicator of the amount of displacement present in the signal. Specifically, when no device displacement is present, the ratio remains consistent and does not change significantly.

The computed ratio is then used to determine 306 the noise type in the PPG signal. If the ratio value changes significantly, the sensor is being displaced and thus displacement noise is present. The corresponding signal data is disregarded (discarded) until the displacement ends. In some embodiments, the noise type decision for the current data point is determined as per If $|R-R\_i|>Thresh*R$ then discard data point where R_i is the ratio value computed for the current data point, Thresh is a pre-determined threshold, and R is the average of the last n (e.g., 10) R_i values of data points that were not discarded. The value of n may be an empirically determined constant.

As is explained in more detail herein, a method used for determining the heart rate estimate extracts each pulse from a buffer of the signal data. If the data points are discarded due to displacement noise, discontinuity in the sequential data corresponding to one or more pulses is created. Accordingly, when data points are discarded, a flag indicating that displacement noise was detected and data points have been discarded is set so that the method can adapt to such discontinuities.

Figure 8:
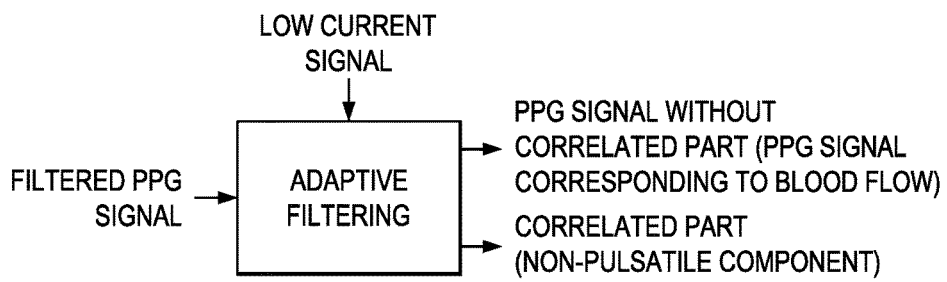
Figure 9:
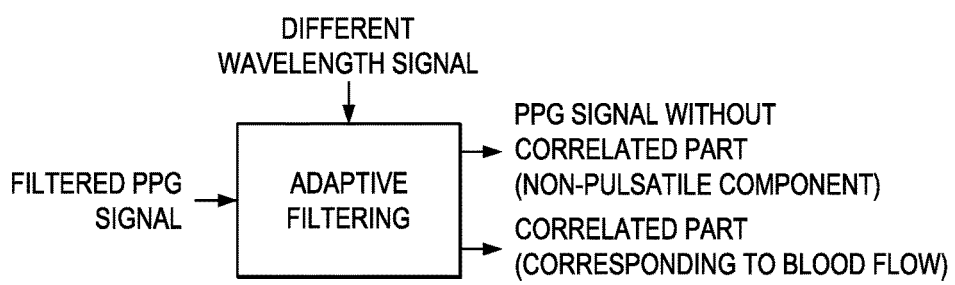

The filtered PPG signal (with those portions corresponding to displacement discarded) is then compensated 308 based on a reference signal for noise introduced by physical movements of a person wearing the monitor unit and/or ambient light. More specifically, the reference signal is used to cancel motion noise in the filtered PPG signal, resulting in a compensated PPG signal. In some embodiments, a method for LED power adjustment noise cancellation as illustrated in FIG. 8 is performed for noise compensation. In some embodiments, a method for complimentary LED wavelength noise cancellation as illustrated in FIG. 9 is performed for noise compensation.

Referring now to FIG. 8, this method for noise cancellation is based on the idea of using a reference signal resulting from reduced current applied to a single LED also used for capturing the PPG signal or reduced current applied to a secondary LED. The light of an LED driven at a lower current than that used to capture the PPG signal will not penetrate the skin to the same extent as the light of an LED driven at "normal" current levels, i.e., current levels sufficient to capture the pulsatile component (the component corresponding the heart pulse). Hence, the resulting reference signal will not include much, if any, of the pulsatile component but will include changes in ambient light conditions as well as artifacts introduced by locomotion (which are also present in the PPG signal).

Figure 10:
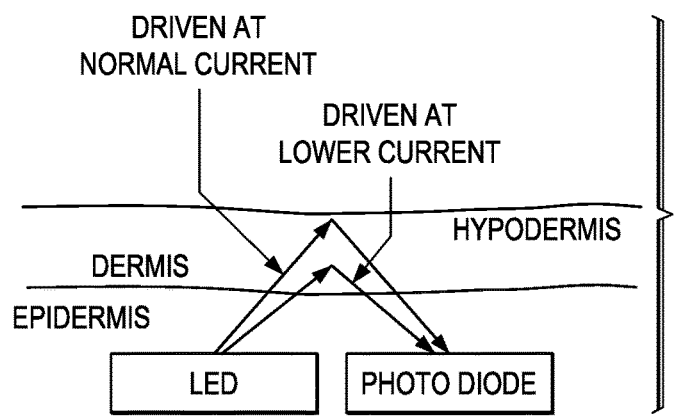
FIGS. 10, 11, 13, 16, 18, and 20 are examples.
Figure 11:
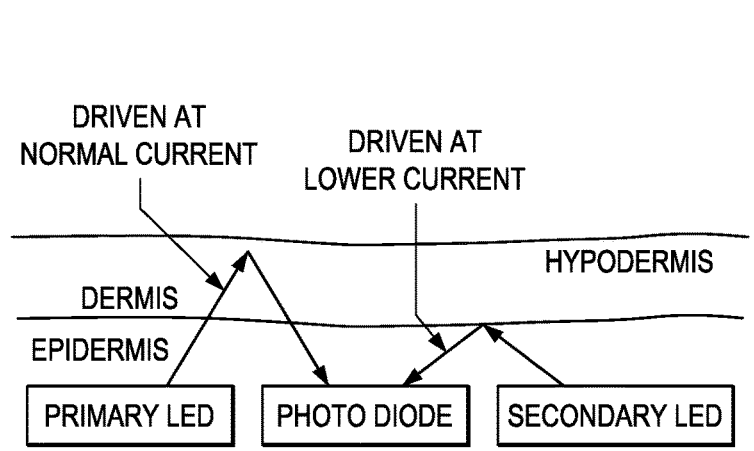

FIGS. 10 and 11 illustrate this concept for, respectively, a single LED embodiment of the PPG sensor 104 and a dual LED embodiment of the PPG sensor 104. For the single LED embodiment, the LED is alternately driven at the normal current by the MCU 108 at time t1 and at a sufficiently lower current at time t2, where t2 follows t1 closely. For the dual LED embodiment, the primary LED at the normal current and the secondary LED at a sufficiently lower current are alternately driven by the MCU 108 at time t1 and t2, where t2 follows t1 closely. More specifically, at time t1, the MCU 108 causes the primary LED to be turned on with the normal current value and the secondary LED is off. At time t2, the MCU 108 causes the current to be removed from the primary LED, thus turning it off, and causes the secondary LED to be turned on with the lower current value. The particular current values used may be determined empirically. The current values needed in a particular implementation may depend on factors such as the particular LED(s) and photodiode used, the relative positions of the LED(s) and the photodiode, and the overall mechanical design of the monitor unit. The normal current may be, for example, 8 mA (milliamps) while the lower current may be 0.05 mA, which is almost two orders of magnitude less than the normal current. The interval between t1 and t2 may also be determined empirically and may depend on factors such as the data collection frequency, the LED duty cycle, and the analog to digital conversion time.

Referring again to FIG. 8, the artifact compensation is performed by applying an adaptive filter to the filtered PPG signal with the lower current signal used as a reference. In general, adaptive filtering refers to dynamically modifying the parameters of a digital filter based on removing a component correlated to the reference signal from the core signal. Any suitable filter approach may be used, such as, for example, a Least Mean Square (LMS) filter. The compensated PPG signal output by this method is the input signal with the correlated part removed.

Referring now to FIG. 9, this method for noise cancellation is based on the idea of using a reference signal resulting from an alternative light wavelength complementary to the wavelength of the LED used for capturing the PPG signal. The second wavelength should carefully selected to have the same level of light absorption by hemoglobin as the wavelength of the primary LED, which means that both LEDs will stimulate a signal with the same pulsatile component.

To generate the PPG signal and the reference signal, the primary LED and the secondary LED are alternately driven by the MCU 108 at time t1 and t2, where t2 follows t1 closely. More specifically, at time t1, the MCU 108 causes the primary LED to be turned on and the secondary LED to be turned off. At time t2, the MCU 108 causes the primary LED, to be turned off and the secondary LED to be turned. The interval between t1 and t2 may be determined empirically and may depend on factors such as the data collection frequency, the LED duty cycles, and the analog to digital conversion time.

The artifact compensation is performed by applying an adaptive filter to the filtered PPG signal with the different wavelength signal used as a reference. In general, adaptive filtering refers to dynamically modifying the parameters of a digital filter based on removing a component correlated to the reference signal from the core signal. Any suitable filter approach may be used, such as, for example, a Least Mean Square (LMS) filter. The compensated PPG signal output by this method is correlated part of the input signal.

Referring again to FIG. 3, either the original filtered PPG signal or the compensated PPG signal is then selected 310 for heart rate estimation based on how much movement intensity is present in the signal. The original filtered PPG signal is considered clean when it contains a low level of movement artifacts and/or device displacement artifacts. Such artifacts are associated with motion of either the hand/arm or the device around the wrist. The signal from the accelerometer 112 is used to differentiate between a clean PPG signal and a PPG signal that contains noise due to the device displacement and/or movement artifacts. More specifically, a measure of movement intensity is estimated from the accelerometer signal, and this measure is used to choose between the two signals. If the intensity measure indicates that movement intensity is low relative to a predetermined intensity threshold, the filtered PPG signal is selected 310; otherwise, the compensated PPG signal is selected. The value of the intensity threshold is implementation dependent and may be determined empirically.

The movement intensity may be estimated 312 from the accelerometer signal as follows. The power of the accelerometer signal is computed and then a linear acceleration is computed based on the power signal. The linear acceleration may be computed by applying an alpha filter to the power signal. A predetermined threshold is then applied to the linear acceleration to determine if the movement is low or high. The value of this threshold may be determined empirically based on collecting movement data from a representative data set.

Figure 12:
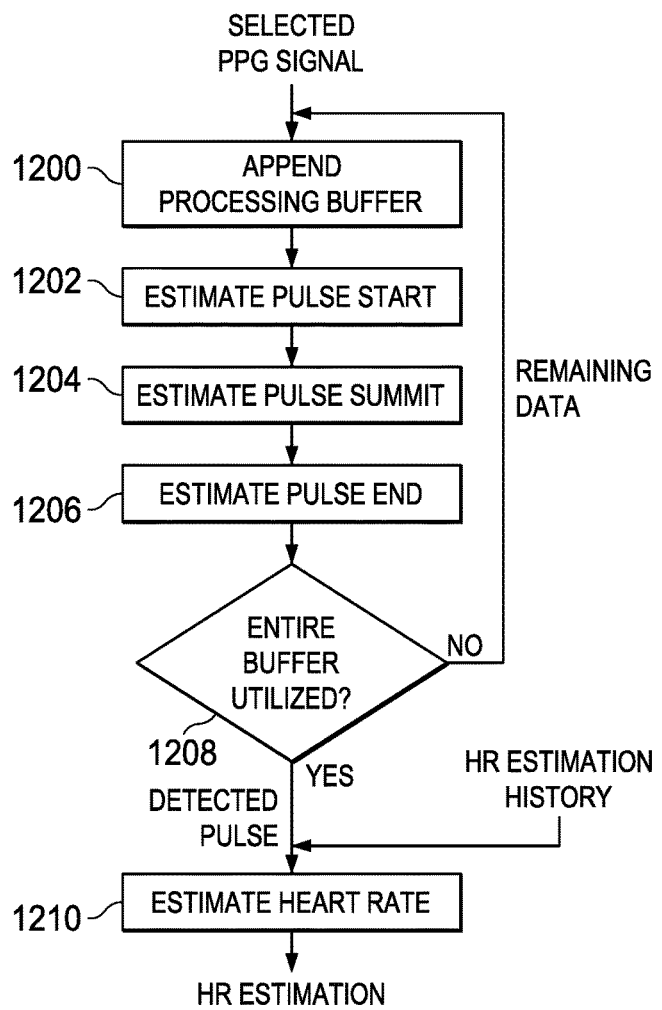

A heart rate estimate is then determined 314 using the selected PPG signal. Any suitable technique for estimating the heart rate from the selected PPG signal may be used. FIG. 12 illustrates one method that may be used. In some embodiments, the estimation processing is performed on a buffer of the signal data that corresponds to 1.5 times the number of points per expected heart beat. For example, initially, the buffer size may be set to 2250 samples, which is 1.5*500*600/20, where 500 Hz is the sampling rate and 20 BPM (beats per minute) is the slowest heart rate the method aims to detect. The size of the buffer may be changed as a better estimation of a heart rate is calculated. The buffer may be maintained in the memory 118 of the monitor unit of FIG. 1.

Figure 13:
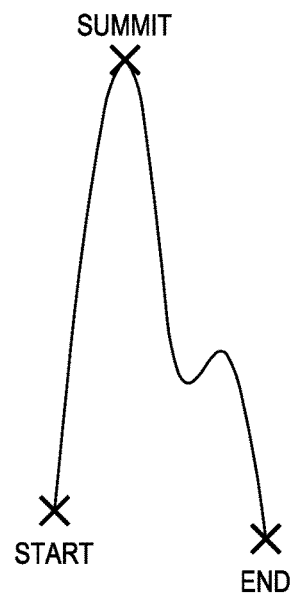

In general, the method attempts to find the start of a heart pulse, the summit or peak of the pulse, and the end of the pulse in the data in the buffer. The visualization of this idea is demonstrated in FIG. 13. The pulse in this figure is a bit simplistic, because such an obvious labeling only occurs in the case of a clean signal, which is simple to process. However, it is meant to provide an intuition of the correspondence of start, summit, and end in the signal. Once the end of the pulse is discovered, the detected pulse is used to estimate the heart rate and any data in the buffer unused in the current pulse is re-used in the next pulse determination iteration. More specifically, in an iteration of heart rate estimation method, sufficient samples from the selected PPG signal are appended 1200 to the buffer to fill the buffer. Note that at the beginning of any iteration except the first, the buffer is not necessarily empty. Rather, it may contain any samples from the previous iteration that were not part of the detected pulse.

Figure 14:
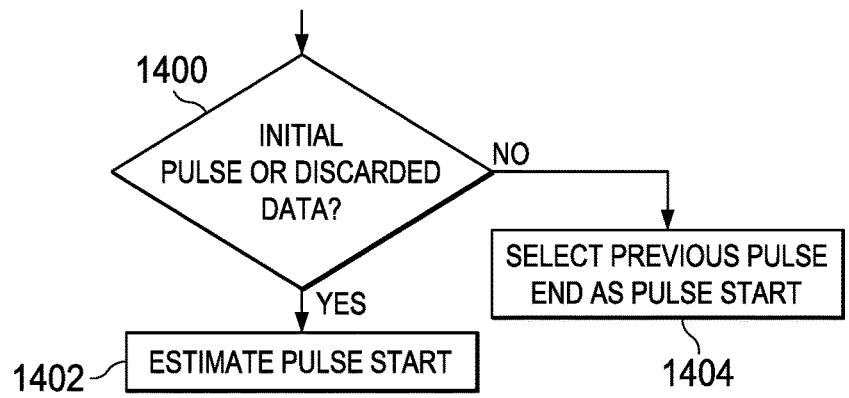

The start of the pulse in the buffered data is then estimated 1202. FIG. 14 is a flow diagram of a method for estimating the start of a pulse. The method begins by determining 1400 whether or not the start of the initial pulse in the signal is to be estimated or if data in the signal has been discarded due to displacement noise. As previously explained, if data is discarded as part of determining the noise type 306 in the PPG signal, a flag is set to indicate this. If either of these cases is true, the start of the pulse is estimated 1402 from the buffer data; otherwise, the end of the pulse determined in the previous iteration is selected 1404 as the start of the current pulse. The start of the pulse may be estimated, for example, by computing the first derivative of the data in the buffer and finding the smallest value (y coordinate) of the first five zero-crossing points of the resulting derivative signal. The sample corresponding to this smallest value is selected as the start of the pulse.

Figure 15:
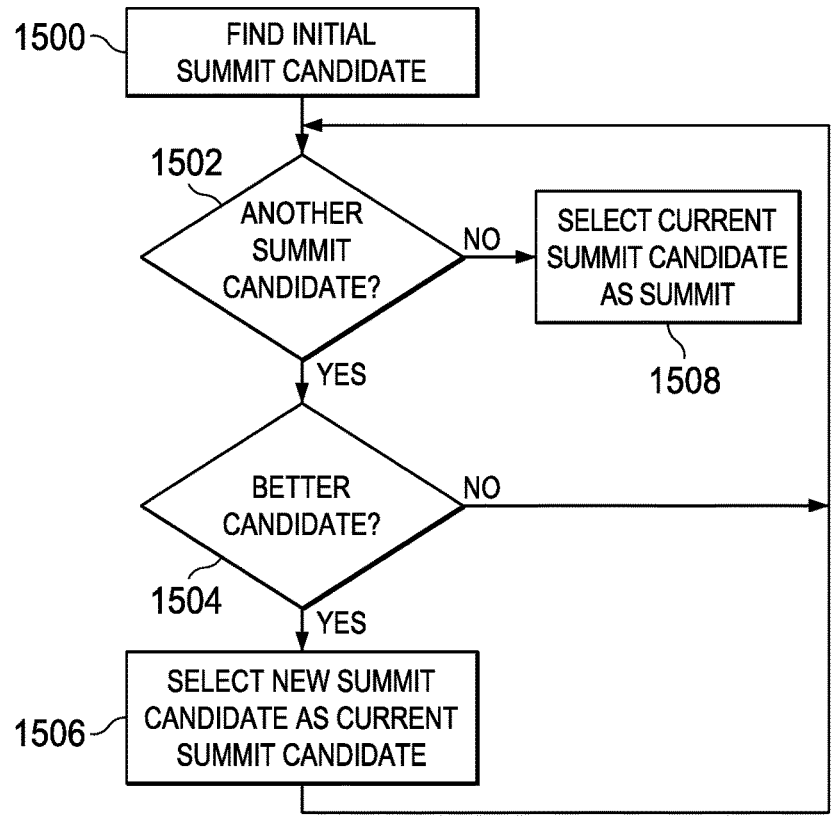

Referring again to FIG. 12, after the pulse start is estimated 1202, the summit of the pulse is estimated 1204. FIG. 15 is a flow diagram of a method for estimating the summit of a pulse. While the summit of a pulse is not directly used in the calculation of the heart rate, it is useful for estimating the end of the pulse. Any pulse can be broken into a transition from the start of the pulse to the summit, and from the summit of the pulse to the end. Treating these two transitions separately, i.e., assuming that the transitions have similar properties but are not identical, is helpful in the context of the noisy data. The transition from the start to the summit represents infusion of the blood in arteries during the heart beat, while the transition from the summit to the end represents diffusion of the blood.

Referring now to FIG. 15, the method beings by determining finding 1500 an initial data point in the buffer that is a candidate for being the summit of the pulse. More specifically, the first local maximum after the pulse start is selected as the initial summit candidate. A local maximum may be determined, for example, as a zero crossing in the first derivative of the data points in the buffer. Next, a check is made to determine 1502 if there is another candidate for the summit. More specifically, the buffered data is checked for another local maximum. Each local maximum in the buffer is a potential candidate for being the peak summit.

If there is another summit candidate 1502, the new candidate is compared to the current summit candidate to determine 1504 if it is a better candidate. If the new summit candidate is the better candidate, the new candidate is selected 1506 as the current summit candidate; otherwise, the current summit candidate remains as the previously selected summit candidate. If there is no other summit candidates in the buffer 1502, then the current summit candidate is selected 1508 as the pulse summit.

Figure 16:
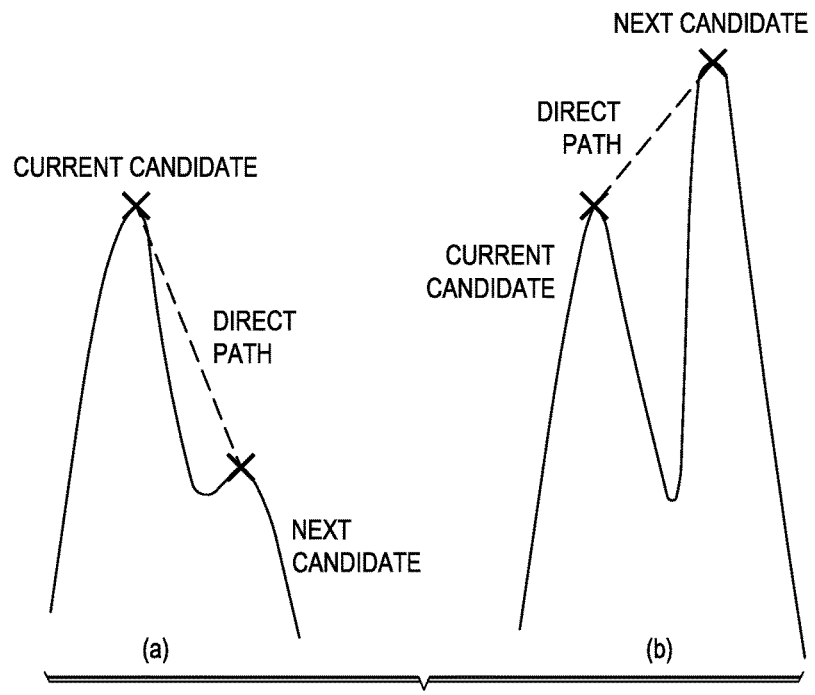

To determine which of two summit candidates is better, the two local maximum points are compared based on the relationship between the direct linear path from the current summit candidate point to the new summit candidate point (as shown in FIG. 16) and the indirect path between the two points tracing the actual signal. If the value (y coordinate) of the new candidate point is both within a factor $\alpha$ of the value of the current candidate point and the length of the direct path between the two points is larger than a factor $\beta$ times the length of the actual path then the new candidate point is considered to be better than the current candidate point. The values of $\alpha$ and $\beta$ used are determined by the quality of the PPG signal. That is, there are values for a and $\beta$ that are used when data from a compensated PPG signal is used for pulse determination and different values for $\alpha$ and $\beta$ that are used when data from a filtered PPG signal are being used for pulse determination. In the case of a compensated (noisy) PPG signal, the values of both parameters are more conservative (larger) than in the case of a filtered (clean) PPG signal. The particular values of $\alpha$ and $\beta$ for compensated and filtered PPG signals may be determined empirically, for example, using a test set of representative noisy and clean PPG signals.

Figure 17:
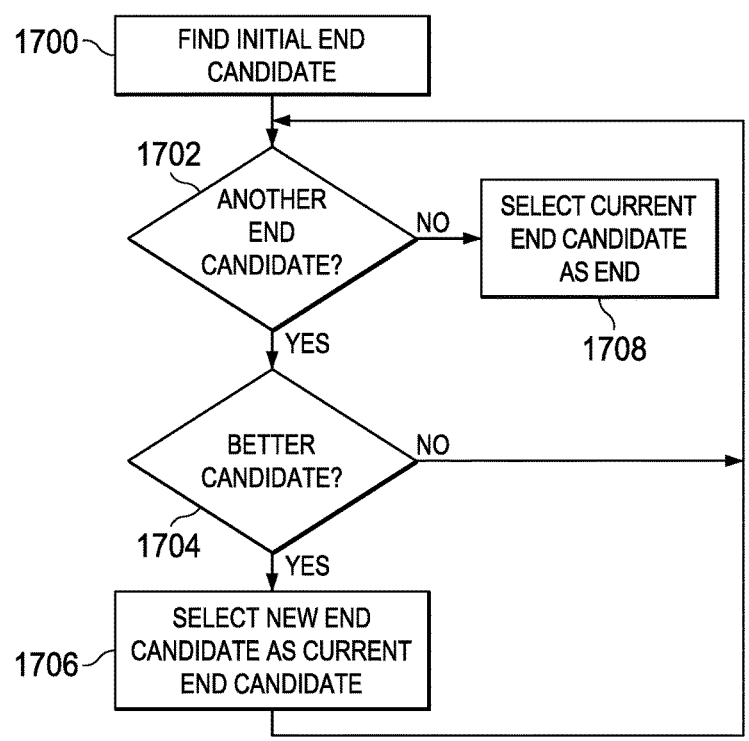

Referring again to FIG. 12, after the pulse summit is estimated 1204, the end of the pulse is estimated 1206. FIG. 17 is a flow diagram of a method for estimating the end of a pulse. The method beings by determining finding 1700 an initial data point in the buffer that is a candidate for being the peak of the pulse. More specifically, the first local minimum after the pulse summit is selected as the initial end candidate. A local minimum may be determined, for example, by analyzing the first derivative of the data points in the buffer for a negative to positive transition. Next, a check is made to determine 1702 if there is another candidate for the end. More specifically, the buffered data is checked for another local minimum. Each local minimum in the buffer (after the summit) is a potential candidate for being the pulse end.

If there is another end candidate 1702, the new candidate is compared to the current end candidate to determine 1704 if it is a better candidate. If the new end candidate is the better candidate, the new candidate is selected 1706 as the current end candidate; otherwise, the current end candidate remains as the previously selected end candidate. If there is no other end candidates in the buffer 1702, then the current end candidate is selected 1708 as the pulse end.

Figure 18:
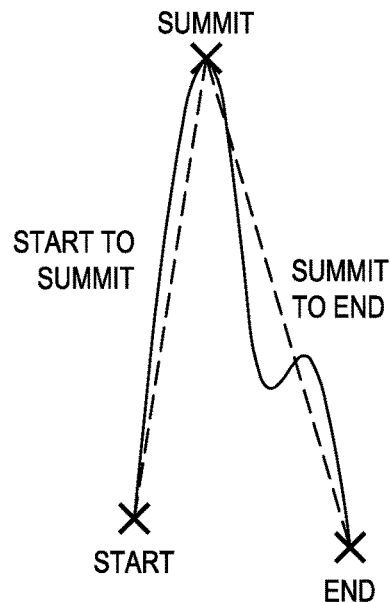

To determine the better candidate between the current end candidate and the new end candidate, a score is computed for each of the candidate end points. The score is determined by the normalized difference between the length of the direct path from the pulse start point to the summit point and the length of the direct path from the summit point to the candidate end point. These paths are illustrated in the example of FIG. 18. If the score of the new end candidate is less than $\mu$ times the score of the current end candidate, the new end candidate is considered to be better than the current end candidate. The value of $\mu$ used is determined by the quality of the PPG signal. That is, there is a value for $\mu$ that is used when data from a compensated PPG signal is used for pulse determination and a different value for $\mu$ that is used when data from a filtered PPG signal are being used for pulse determination. In the case of a compensated (noisy) PPG signal, the value is lower than in the case of a filtered (clean) PPG signal. The particular values $\mu$ for compensated and filtered PPG signals may be determined empirically, for example, using a test set of representative noisy and clean PPG signals. The motivation behind this scoring system is to allow for the possibility that the beginning and the end of a heart pulse will not have the same y coordinate, i.e., the signal is not strictly sinusoidal but will drift up and down over time. This approach assumes that if the blood saturation or de-saturation becomes slower, it will take a longer period of time for the blood to flow through.

Figure 19:
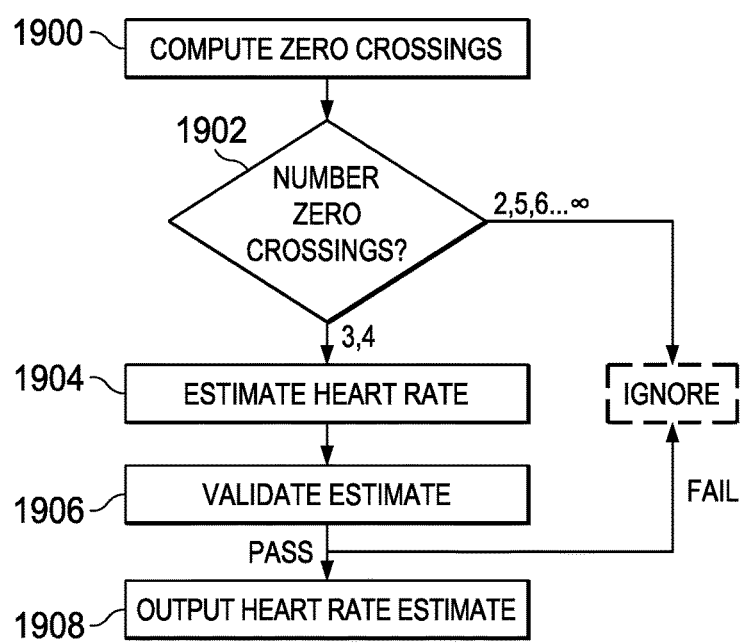
Figure 20:
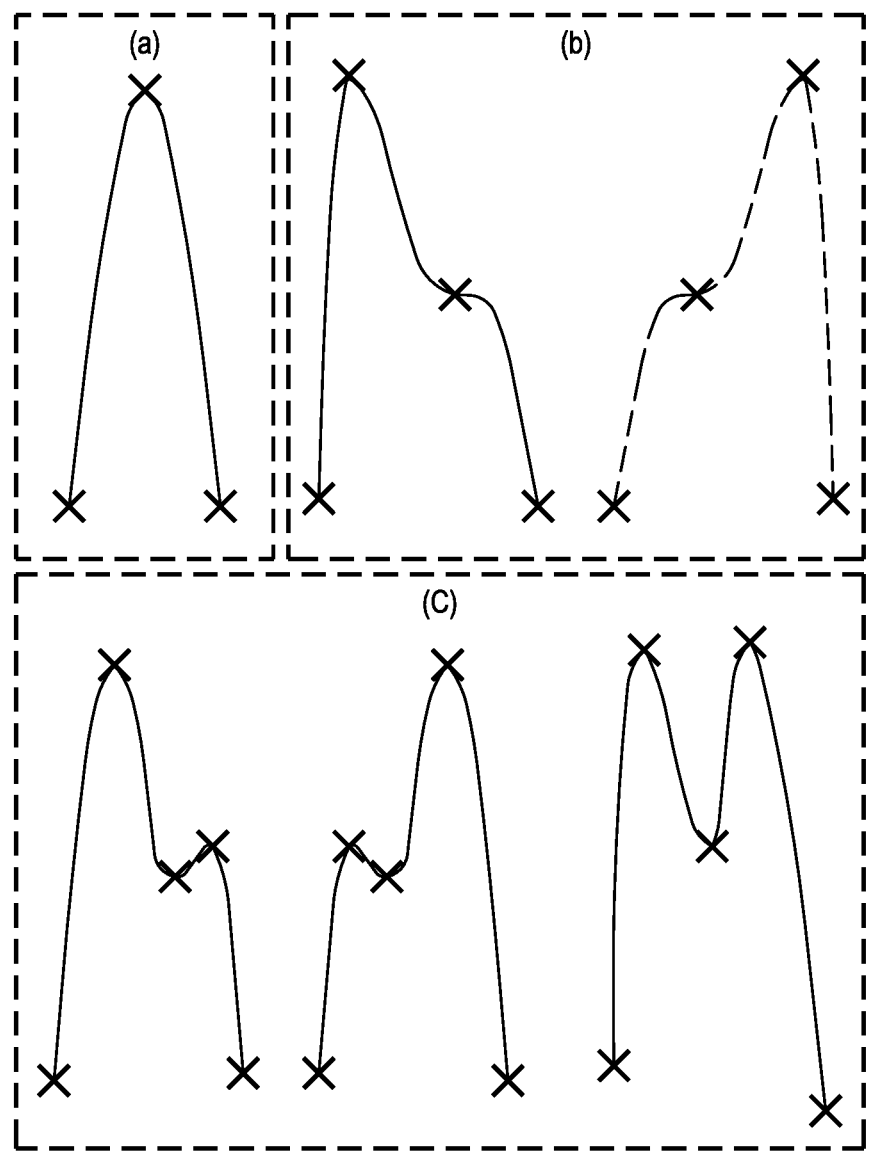

Referring again to FIG. 12, after the pulse start, summit, and end are determined, the heart rate is estimated 1210. FIG. 19 is a flow diagram of a method for estimating heart rate. As was previously mentioned, all identified pulses are not included in the heart rate estimation. Rather, the quality of a pulse is evaluated to determine whether or not the pulse is to be used for heart rate estimation. To understand the properties of PPG signals, the morphology of such signals should be considered. FIG. 20 shows examples of basic morphologies of PPG signals in terms of the zero crossing points. Example (a) shows a pulse that contains 3 zero crossing points. A pulse is likely to be similar to this example in the case of a perfectly clean filtered signal. Note that relative displacement is likely to produce a similar shape. However, the noisy signal will have a large slope, which means that the pulse duration will be short in the noisy signal. Example (b) shows pulses with four zero-crossing points. These are very particular signal shapes that generally correspond to a clean pulse in both clean and noisy signals. A contaminated version of the same pulse is likely to gain a fifth zero crossing point, as illustrated in the left plot of example (c). While the left and middle plots of example (c) correspond to clean pulses, they cannot be differentiated from the pulse of the rightmost plot. The right plot could be a set of two pulses with a DC drift in the middle in case of a clean signal, or a movement contaminated signal in a noisy signal.

Referring now to FIG. 19, the method begins by computing 1900 the number of zero crossings between the start and end of the detected pulse. If the number of zero crossings found 1902 is three or four, the pulse is used to estimate 1904 the heart rate. If the number of zero crossings found 1902 is two or greater than four, the detected pulse is not used to estimate the heart rate. The heart rate may be estimated 1904 as the data collection frequency (in samples per second) multiplied by 60 seconds and divided by the pulse duration (in data points per beat).

After the heart rate is estimated 1904, estimation validation 1904 is performed to decide whether or not the heart rate estimate is good. The estimation validation is based on the assumption that the heart rate cannot change instantaneously. In general, the estimation validation verifies whether or not the heart rate estimate is consistent with previous estimates. If the pulse passes this estimation validation, the heart rate estimate is output 1908 for further processing such as, for example, transmission to another device for display and/or analysis.

The estimation validation may be based on an assumption that the heart rate will not change by more than 10 beats per second (bps) and may be performed as follows. Given a new pulse, compute the elapsed time since the last valid heart rate estimation. For example, if no pulses have been ignored or produced a heart rate estimate that failed the sanity check since the last valid heart rate estimation, then the duration of the pulse is the elapsed time. If one or more pulses have been ignored or produced a heart rate estimate that failed the sanity check between the current pulse and the last valid heart rate estimation, then the elapsed time is the duration of those pulses plus the duration of the current pulse. The 10 bps is then scaled with respect to the computed elapsed time. If the new heart rate estimate is less than the sum of the previous valid heart rate estimate and the scaled 10 bps threshold, the current heart rate estimate passes the estimation validation.

Other Embodiments

While the invention has been described with respect to a limited number of embodiments, those skilled in the art, having benefit of this disclosure, will appreciate that other embodiments can be devised which do not depart from the scope of the invention as disclosed herein.

For example, while embodiments have been described here in reference to a watch-like form factor, one of ordinary skill in the art will understand that embodiments of the heart rate measurement methods described herein may be used in PPG heart rate monitor units housed in form factors suitable for monitoring heart rate in locations on the body of a person such as, for example, the forehead, an ear lobe, a finger, and an upper arm.

In another example, one of ordinary skill in the art will understand embodiments in which a motion sensor other than an accelerometer is used.

In another example, one of ordinary skill in the art will understand embodiments in which a light detector other than a photodiode is used, such as, for example a photoresistor or a phototransistor. Further, one of ordinary skill in the art will understand two LED embodiments in which two light detectors are used, one for each LED.

In another example, one of ordinary skill in the art will understand embodiments having more LEDs and/or light detectors than the example embodiments described herein. Further, one of ordinary skill in the art will understand embodiments in which the LEDs and/or light detectors may have different positions and orientations on a monitoring device than the examples described herein.

In another example, one of ordinary skill in the art will understand embodiments in which the photodiode has an optical filter such as, for example, a film that restricts the type of light that the photodiode observes to infrared.

The methods described herein may be implemented in hardware, software, firmware, or any combination thereof. If completely or partially implemented in software, the software may be executed in one or more processors, such as a microcontroller, microprocessor, application specific integrated circuit (ASIC), field programmable gate array (FPGA), or digital signal processor (DSP). The software instructions may be initially stored in a computer-readable medium and loaded and executed in the processor. In some cases, the software instructions may also be sold in a computer program product, which includes the computer-readable medium and packaging materials for the computer-readable medium. In some cases, the software instructions may be distributed via removable computer readable media, via a transmission path from computer readable media on another digital system, etc. Examples of computer-readable media include non-writable storage media such as read-only memory devices, writable storage media such as disks, flash memory, memory, or a combination thereof.

Although method steps may be presented and described herein in a sequential fashion, one or more of the steps shown in the figures and described herein may be performed concurrently, may be combined, and/or may be performed in a different order than the order shown in the figures and/or described herein. Accordingly, embodiments should not be considered limited to the specific ordering of steps shown in the figures and/or described herein.

It is therefore contemplated that the appended claims will cover any such modifications of the embodiments as fall within the true scope of the invention.

What is claimed is:

1. A method performed by a photoplethysmograph (PPG) heart rate monitor device, the method comprising:
    receiving an accelerometer signal from a motion sensor of the heart rate monitor device;
    capturing a PPG light signal, in which the PPG light signal is:
        filtered when the accelerometer signal is below a threshold; or
        motion compensated when the accelerometer signal is above the threshold;
    detecting a pulse in a portion of the filtered or motion compensated PPG light signal, including detecting a start point of the pulse;
    determining a summit point and an end point of the pulse based on the start point of the pulse, in which determining the summit point includes:
        determining a first maximum point within a first portion of the pulse;
        determining a second maximum point after the first maximum point;
        determining a direct linear path difference between the first maximum point and the second maximum point;
        determining an indirect path difference between the first maximum point and the second maximum point; and
        selecting the summit point as either the first maximum point or the second maximum point based on a comparison of the direct linear path difference and the indirect path difference;
    estimating a pulse rate based on the start point, the summit point, and the end point; and
    outputting the estimated pulse rate to another device.

2. The method of claim 1, wherein the selecting the summit point includes:
    selecting the first local maximum point as the summit point when the direct linear path difference does not exceed the indirect path difference by a predetermined factor; and
    selecting the second local maximum point as the summit point; when the direct linear path difference exceeds the indirect path difference by the predetermined factor.

3. A method performed by a photoplethysmograph (PPG) heart rate monitor device, the method comprising:
    receiving an accelerometer signal from a motion sensor of the heart rate monitor device;
    capturing a PPG light signal, in which the PPG light signal is:
        filtered, when the accelerometer signal is below a threshold; or
        motion compensated, when the accelerometer signal is above the threshold;
    detecting a pulse in a portion of the filtered or motion compensated PPG light signal, including detecting a start point of the pulse;
    determining a summit point and an end point of the pulse based on the start point of the pulse, wherein determining the end point includes:
        determining a first local minimum point after the summit point of the pulse;
        determining a second minimum point after the first minimum point;
        determining a first path between the summit point and the first minimum point;
        determining a second path between the summit point and the second minimum point; and
        selecting the end point as either the first minimum point or the second minimum point based on a comparison of the first path and the second path;
    estimating a pulse rate based on the start point, the summit point, and the end point; and
    outputting the estimated pulse rate to another device.

4. The method of claim 3, wherein the selecting the end point includes:
- determining a first normalized difference between a first length and a second length of the first minimum point, wherein:
  - the first length is measured between the start point and the summit point; and
  - the second length is measured between the summit point and the first minimum point;
- determining a second normalized difference between a first length and a second length of the second minimum point, wherein:
  - the first length is measured between the start point and the summit point; and
  - the second length is measured between the summit point and the second minimum point; and
- comparing the first normalized difference with the second normalized difference.

5. The method of claim 4, wherein the selecting the end point includes:
- selecting the first minimum point as the end point when the second normalized difference is greater than a predetermined multiple of the first normalized difference; and
- selecting the second minimum point as the end point when the second normalized difference is less than the predetermined multiple of the first normalized difference.

* * * * *